United States Patent [19]

Schubert et al.

[11] Patent Number: 5,202,298
[45] Date of Patent: Apr. 13, 1993

[54] PROCESS FOR PREPARING CARBONATE SUPPORTS AND CATALYSTS

[75] Inventors: Paul F. Schubert, Sunnyvale, Calif.; Ralph E. Bonnell, Dewey, Okla.; Norman L. Freeman, Jr., Oologah, Okla.; Denton C. Fentress; Kent E. Mitchell, both of Bartlesville, Okla.; Richard E. Lowrey, Muscatine, Iowa; Donald H. Kubicek; Warren M. Ewert, both of Bartlesville, Okla.

[73] Assignee: Phillips Petroleum Company, Bartlesville, Okla.

[21] Appl. No.: 624,800

[22] Filed: Dec. 5, 1990

[51] Int. Cl.$^5$ ................ B01J 27/232; B01J 23/04
[52] U.S. Cl. .................. 502/174; 423/421; 502/439; 585/516
[58] Field of Search .......... 502/174; 423/421

[56] References Cited

U.S. PATENT DOCUMENTS

| | | | |
|---|---|---|---|
| 3,168,524 | 2/1965 | Mahan et al. | 260/290 |
| 3,862,207 | 1/1975 | Csomontanyi et al. | 252/470 |
| 4,134,858 | 1/1979 | Courty | 252/455 R |
| 4,533,781 | 8/1985 | Matsuno et al. | 585/516 |
| 4,544,790 | 10/1985 | Drake | 585/516 |
| 4,560,769 | 12/1985 | Menig et al. | 548/560 |
| 4,595,787 | 6/1986 | Drake | 585/516 |
| 4,609,637 | 9/1986 | Drake | 502/174 |
| 4,656,154 | 4/1987 | Drake | 502/185 |
| 4,661,466 | 4/1987 | Drake et al. | 502/184 |
| 4,687,877 | 8/1987 | Bartley et al. | 585/516 |
| 4,727,213 | 2/1988 | Drake et al. | 585/511 |
| 4,729,982 | 3/1988 | Thistlethwaite et al. | 502/338 |
| 4,774,215 | 9/1988 | Drake et al. | 502/174 |
| 4,810,688 | 3/1989 | Ewert et al. | 502/174 |
| 4,895,819 | 1/1990 | Drake | 502/174 |
| 4,950,632 | 8/1990 | Drake | 502/184 |
| 5,081,093 | 1/1992 | Hasselbring | 502/174 |

*Primary Examiner*—Paul E. Konopka
*Attorney, Agent, or Firm*—Lynda S. Jolly

[57] ABSTRACT

Catalyst supports, catalyst systems, methods for the preparation thereof, and dimerization process therewith are provided catalyst supports are extruded from a thick paste of potassium carbonate and water catalyst systems comprise at least one elemental alkali metal deposited on the catalyst sypport. Optionally, the catalyst system further comprises at least one promoter.

19 Claims, No Drawings

PROCESS FOR PREPARING CARBONATE SUPPORTS AND CATALYSTS

BACKGROUND OF THE INVENTION

This invention relates to alkali metal carbonate supported alkali metal catalysts.

It is known in the art to employ alkali metal carbonate supported alkali metal catalysts for such conversions as propylene dimerization. It is also known in the art to prepare alkali metal carbonate catalyst supports by making a thick paste in a liquid and eventually forming a pelletized, tabletted, or granular support. The support prepared in such a manner subsequently can be treated with an elemental alkali metal to form a catalyst system. Alkali metal carbonate catalyst supports prepared from a water-based paste are difficult to process because the alkali metal carbonate to water ratio must be closely controlled or the paste can have the wrong consistency and be unworkable. Additionally, all of the mixing and drying conditions must be carefully controlled in order to form a useable support. Extrusion of an alkali metal carbonate and water paste is much more efficient than forming individual pellets or tablets, but is extremely complex because of either high solubility of higher molecular weight alkali metal carbonates or the low solubility of lower molecular weight alkali metal carbonates in water. Thus, it is difficult to process and easily form a useable catalyst support from an alkali metal carbonate and water.

SUMMARY OF THE INVENTION

It is an object of this invention to provide a process to easily prepare a potassium carbonate catalyst support.

It is a further object of this invention to provide an easily processed potassium carbonate catalyst support.

It is yet another object of this invention to provide a method to prepare an improved potassium carbonate supported elemental alkali metal catalyst system.

It is yet a further object of this invention to provide an improved catalyst system for the dimerization of olefins.

It is yet another object of this invention to provide an improved process for the dimerization of olefins.

In accordance with the present invention, a potassium carbonate catalyst support is prepared from a thick paste comprising potassium carbonate and water. The resultant thick paste is extruded into an extrudate product, dried, and calcined to give a catalyst support. Additionally, at least one elemental alkali metal can be contacted with the extruded support to form an olefin dimerization catalyst system.

DESCRIPTION OF THE PREFERRED EMBODIMENTS

The present invention provides a process to prepare a catalyst support which comprises the steps of forming a thick paste comprising potassium carbonate and water, and extruding said paste to form an extrudate. In order to form a catalyst support, the extrudate then must be dried and subsequently calcined.

In accordance with yet another embodiment of the invention, the previously prepared extruded potassium carbonate catalyst support can be contacted with at least one elemental alkali metal to produce a catalyst composition which is useful to dimerize olefins.

In accordance with yet a further embodiment of the invention, the potassium carbonate catalyst support and the elemental alkali metal catalyst composition can be contacted with at least one promoter.

Supports

Commerically available potassium carbonate, in the form of powder, granules, or the like, is mixed with water to form a thick paste. The support must be prepared from potassium carbonate in order to be able to extrude a water/potassium carbonate mixture that forms a useful catalyst support. Other alkali metal carbonates are either too insoluble or too soluble in water to be used easily in an extrusion process. Additionally, a potassium carbonate support is more easily impregnated with an elemental alkali metal than other supports.

As used in this disclosure, the term "support" refers to a carrier for another catalytic component. However, by no means, is the support necessarily an inert material; it is possible that the support can contribute to catalytic activity and selectivity.

In order to be able to extrude a water/potassium carbonate mixture, the final ratio of water to potassium carbonate during the extrusion process is critical. Generally, the mass ratio (gram/gram) during extrusion of water to potassium carbonate is within the range of about 0.23 to about 0.29, when using dried potassium carbonate, and preferably within the range of about 0.24 to about 0.28. Most preferably, the water to potassium carbonate weight ratio is within the range of about 0.25 to about 0.27 grams of water per grams potassium carbonate in order to provide a consistent, durable catalyst support which can be used to obtain high selectivity, high olefin conversion, and a high ratio of desired isomers to undesired isomers.

The water to potassium carbonate ratio during the extrusion process can also be expressed in terms of moles of water per mole of potassium carbonate. Generally a molar ratio within the range of about 1.8 (i.e., 1.8 moles of water per mole of potassium carbonate) to about 2.2 is used during extrusion, preferably within the range of about 1.8 to about 2.1. Most preferably, for the reasons given above, a molar ratio of water to potassium carbonate is within a range of about 1.9 to about 2.1. If too much water is used, the potassium carbonate can completely dissolve and be unextrudable. If too little water is used, the paste will not extrude either because it is too dry or too thick.

Preferably, in order to better control temperature, since the reaction between water and potassium carbonate is exothermic, and to prepare a porous extrudate with an appropriate pore size distribution, the water is pre-mixed with a minor amount of potassium carbonate to form a dilute aqueous potassium carbonate solution prior to contacting the major portion of the potassium carbonate. Any source can be used for the minor amount of potassium carbonate which is pre-mixed with the water. For example, commercially available new potassium carbonate can be used. Other sources include, but are not limited to, catalyst support waste material, i.e., non-usable support material generated during the support preparation process, such as, for example, dried and/or calcined fines; off-specification catalyst support; and/or catalyst support. Usually, the concentration of the dilute potassium carbonate solution is at least about 0.001M (0.001 moles $K_2CO_3$/liter $H_2O$) and preferably within the range of about 0.002M to about 0.01M, for the reasons stated above.

Preferably, although not required, mixing occurs as the liquid, i.e., water, or dilute water/potassium carbonate solution, is being added to the potassium carbonate. The liquid is added to the potassium carbonate in such a manner so as to affect thorough contacting of the water and potassium carbonate. Good liquid/carbonate mixing occurs if the liquid is not poured, but is distributed evenly over the potassium carbonate. Most preferably the liquid is sprayed onto the potassium carbonate for best contacting.

The amount of time used to add the liquid is any amount of time necessary to effect thorough contacting of the liquid and potassium carbonate. However, the liquid addition time can vary with the volume of liquid and mass of potassium carbonate used. For example, when preparing up to about 100 pounds of catalyst support, liquid addition times up to about one hour is sufficient, preferably within the range of about 3 to about 15 minutes. Most preferably, times within the range of about 3 to about 6 minutes are used for best mixing and contacting. Faster, more rapid, addition times are preferred so that all of the liquid and potassium carbonate can be contacted nearly simultaneously and, thus, forming a better, more durable, catalyst support.

After the liquid is added to the potassium carbonate, additional mixing, or mulling, is not necessary, but preferably some additional mixing occurs. Once again, the additional mix time can vary with the quantity of potassium carbonate and liquid combined. Generally, when preparing up to about 100 pounds of support, the mulling time, after all the liquid is added, can be up to about 1 hour, and preferably within the time range of about 10 minutes to about 1 hour. Most preferably, the additionally mixing time is within the range of about 10 to about 40 minutes, in order to ensure that the potassium carbonate reaction with water is complete, for good extrusion rates, and to give a consistent ratio of desired to undesired isomer products.

Although additional mixing time is preferred, the entire additional mixing time usually is not considered active mixing time. As defined in this disclosure, mixing time is the contact time of liquid and potassium carbonate, i.e., mixer residence time. Active mixing time is the mixing time, expressed in terms of percent, wherein the mixer, or muller, is actually operating. Usually, the liquid/potassium carbonate is actively mixed for about 1 to about 50 percent of the time, preferably for about 1 to 40 percent of the total mixing the time. Preferably, the liquid/potassium carbonate is actively mixed for about 5 to about 20 percent of the time for good liquid/solid contacting and to maintain potassium carbonate particle integrity.

The temperature of the liquid and newly formed thick paste during the liquid addition and subsequent mixing generally is maintained at or below room temperature, and preferably is within the range of about 0° to about 10° C. Most preferably, the temperature during mixing is within the range of about 0° to about 5° C. High temperatures can cause increased dissolution of the potassium carbonate, which can cause the dried extrudate to be less porous, and therefore less suitable as a catalyst support. Low temperatures, i.e., below the freezing point of water, can cause solidification of the thick paste.

After liquid addition and the water/potassium carbonate mulling, the paste optionally can be aged. Generally, aging times of greater than 24 hours do not produce any additional benefits. Preferably, the paste is aged for times within the range of about 0 to about 8 hours and most preferably for times within the range of about 0 to about 2 hours. Longer aging times tend to improve extrusion rates, but long aging times also tend to slow production and can be uneconomical.

Once the liquid/potassium carbonate thick paste is prepared, i.e., mulled and, if desired, aged, the thick paste is then ready for extrusion. The paste can be formed into an extrudate using an extruder. The extrudate can be any diameter, but for best catalytic activity and ease of handling and processability, the extrudate is from about 1/16 to about ¼ inch in diameter. Larger or smaller diameter extrudates can be prepared, depending on the desired use of the resultant extrudate. After the extrudate passes through the extruder dye, the extrudate can be cut into uniform lengths, if desired. However, uniform lengths are not always necessary, so the extrudate can be allowed to break on its own, into any lengths. If the extrudate is allowed to break on its own, it will usually have a length of about 2 to about 7 times the diameter width. Usually, the extrudate is allowed to break of its own accord because of ease of manufacture and economics.

In order to prepare a catalyst support that can be easier to impregnate with an elemental alkali metal, the barrel temperature of the extruder should be closely controlled. Generally, extruder barrel temperatures within the range of about 0° to about 60° C. are acceptable, although the temperature range can vary based on the subsequent drying process. For example, if the extrudate is to be vacuum dried, extruder barrel temperatures within the range of about 10° to about 30° C. are preferred and most preferably temperatures within the range of about 20° to about 30° C. are used. If a convection drying process is to be used, preferably, the extruder barrel temperatures are within the range of about 20° to about 60° C., and most preferably within the range of about 20° to about 50° C. Lower temperatures usually result in easier elemental alkali metal impregnation; higher temperatures can inhibit elemental alkali metal impregnation.

The extrusion rate, expressed in terms of mass of extrudate produced per unit time, i.e., pounds per minute, depends on many factors, such as, for example, particular equipment used, water level, mixing time, extruder auger speed, and/or aging time. For example, a higher auger speed (expressed in terms of rotations per minute, rpm) will increase the extrusion rate. However, if the auger rpm is too fast or too slow, the extruder can become plugged. Therefore, it is desirable to increase auger rpm, but not at the expense of plugging the extruder and/or producing poor extrudate. When using a large, single screw extruder, such as, for example, a 2¼ inch Bonnot single screw extruder, the extruder auger rpm is preferably within a range of from about 20 to about 100 rpm, preferably within a range of from about 30 to about 80 rpm. Most preferably, for the reasons given above, the extruder auger rpm, when using a large single screw extruder, is within a range of from about 45 to about 70 rpm.

Once the extrudate is formed, the extrudate can be dried and calcined according to any manner known in the art. Exemplary methods of drying include, but are not limited to, static drying, microwave drying, freeze drying, vacuum drying, and/or convection drying. For ease of use and due to ready availability, vacuum drying and/or convection drying are preferred drying methods.

If vacuum drying of the extrudate is employed, generally the drying temperatures are within the range of about 145° to about 170° C., and preferably within the range of about 145° to about 165° C. Most preferably, temperatures within the range of about 145° to about 160° C. are used in order to maintain the integrity of the support. Higher drying temperatures can cause fracturing of the extrudate particles and therefore unacceptable fines, and lower temperatures can result in ineffective moisture removal. Generally, the vacuum drying process is considered complete when the extrudate moisture content is within the range of about 0 to about 3 weight percent water, based on the total weight of the extrudate, and preferably within the range of about 0 to about 2 weight percent water. Most preferably, the final moisture content is within the range of about 0 to about 1 weight percent water in order to facilitate elemental alkali metal impregnation. Too high of a residual moisture content makes the subsequent calcination more difficult, and can inhibit the subsequent elemental alkali metal impregnation.

If convection drying of the extrudate is employed, generally drying temperatures within the range of about 100° to about 260° C. are used, and preferably temperatures within the range of about 120° to about 230° C. are used. Most preferably, temperatures within the range of about 145° to about 205° C. are used in order to maintain the integrity of the support, as well as the reasons regarding vacuum drying. Generally, the convection drying process is considered complete when the extrudate moisture content is within the range of about 0 to about 10 weight percent water, based on the total weight of the extrudate, and preferably within the range of about 0 to about 6 weight percent water. Most preferably the final moisture content is within the range of about 0 to about 3 weight percent water in order to facilitate elemental alkali impregnation. Since drying is more economical than the subsequent step of calcining, preferably as much water as possible is removed during the drying step.

Preferably, the support is convection dried. Convection drying is more economical than vacuum drying. More importantly, the surface of a convection-dried support is different from a vacuum-dried support. A convection-dried support has more large pores penetrating the thick wall, or shell, of the potassium carbonate extrudate at the edge of the extrudate; a vacuum-dried extrudate has far fewer pores. After the subsequent calcination step, the shell of a convection-dried, extruded support seems to disappear, and interior and exterior potassium carbonate particles are nearly indistinguishable; and the surface appears rough, similar to dried foam. The shell of a vacuum-dried, extruded support, after calcination, remains thick and distinct; the surface is smooth except for deep fractures and fissures where the few pores were originally visible. This difference in the surface affects the ease of elemental alkali metal impregnation. A convection-dried support can be easier to impregnate than a vacuum-dried support.

The drying atmosphere can be any type of atmosphere. For ease of use and economics, the preferred drying ambient is air.

After the extrudate is dried, it is then calcined to remove any residual water. Calcining, like drying, can be done in any atmosphere. For ease of use and economics, air is the preferred atmosphere. However, if drying or calcining is done in an inert atmosphere and the support is maintained and stored in an inert atmosphere, the amount of oxygen carried into the elemental alkali metal impregnation step can be reduced, thus making the elemental alkali metal impregnation easier and more efficient. Another optional method to minimize exposure to air and for economic efficiency is to perform the drying and calcining processes in the same apparatus, i.e., the same oven, heater, or dryer.

Calcining temperatures and times are interdependent. For example, higher temperatures require shorter calcination times and lower calcination temperatures require longer heating times. Preferably, for economic reasons, lower temperatures and short calcination times are preferred, when possible. Usually, temperatures within the range of about 200° to about 400° C. are employed for calcination, and preferably temperatures within the range of about 230° to about 350° C. are used. Most preferably, for economic reasons, temperatures within the range of about 250° to about 350° C. are used. The calcination time can be any amount of time sufficient to remove substantially all of the water in the support. Generally, calcination times of up to about 5 hours are sufficient, preferably times within the range of about 5 minutes to about 3 hours are employed. Most preferably, times within the range of about 15 minutes to about 3 hours are used.

The potassium carbonate support can contain additional components which do not adversely affect the extrusion process or the subsequent drying or calcining steps. For example, pigments, dyes, processing aids, inert fillers, and/or binders can be added. Graphite, or any form of a carbonaceous compound, should not be added to the support prior to support calcining unless it is fully removed during calcining; a carbonaceous compound can have detrimental effects on the catalyst system. For example, the catalyst system wherein the support contains a carbonaceous compound, can fracture and/or disintegrate during the dimerization process due to formation of carbon-alkali metal intercalation compounds.

Catalysts and Promoters

Catalysts systems employed in the practice of this invention comprise one of the potassium carbonate supports described above, at least one elemental alkali metal catalyst, and optionally one or more of the following additional promoters:

a carbonaceous compound,
elemental copper,
elemental cobalt,
finely divided stainless steel,
finely divided glass, and
mixtures of two or more thereof.

It should be recognized, however, that the catalyst systems of the invention can contain additional components which do not adversely affect the catalyst performance, such as, for example, pigments, dyes, processing aids, inert fillers, binders, and the like.

The alkali metals contemplated to be within the scope of the invention include lithium, sodium, potassium, rubidium, cesium, and mixtures thereof. While the proportion of alkali metal combined with the potassium carbonate support can vary appreciably, generally at least about one weight percent of alkali metal based on the total weight of calcined support will be employed. Generally, about 1 to about 20 weight percent alkali metal will be employed with about 2 to about 15 weight percent preferred. An alkali metal loading of about 3 to about 10 weight percent based on the total weight of calcined support is most preferred for most efficient use of reagents, high catalyst activity and selectivity, and ease of catalyst preparation. Potassium is the preferred elemental alkali metal due to its ready availability, good catalytic activity and selectivity, as well as ease and safety in handling.

However, some elemental sodium can be combined with the potassium. The addition of sodium to potassium can be beneficial in that the elemental alkali metal impregnation temperature can be lowered. For example, a mixture of up to about 25 weight percent sodium/75 weight percent potassium does not harm selectivity or activity, but greater than about 25 weight percent sodium can adversely affect the catalyst system. Preferably, if using a sodium/potassium mixture to impregnate the support, the mixture will comprise from about 0.01 to about 10 weight percent sodium, with the balance being potassium, for the most beneficial effects.

The proportion of optional promoter on the potassium carbonate support can vary appreciably, but generally, at least one weight percent of the optional promoter based on the total weight of treated support will be employed. Usually, if the promoter is elemental cobalt or finely divided glass, not more than 50 weight percent will be used. With elemental copper, usually not more than about 30 weight percent will be used and usually not more than about 80 weight percent finely divided stainless steel will be used, all based on the total weight of treated support employed.

The general procedure for preparation of the catalyst systems, after calcining the support, of the invention involves heating the potassium carbonate support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in an oxygen-free atmosphere, is preferably carried out with suitable mixing to ensure even distribution. Suitable temperatures for the contacting step will vary with the particular alkali metal employed. For example, with elemental potassium, temperatures in the range of about 80° to 100° C. are preferred, while with elemental sodium, temperatures in the range of about 100° to 140° C. are preferred.

While the alkali metal treated support is maintained at or above the melting point of the particular alkali metal used, in an oxygen-free atmosphere, any desired promoter(s), such as for example, finely divided stainless steel or elemental copper, can be gradually added while the treated catalyst is continuously stirred. For example, with potassium, temperatures in the range of about 80° to about 100° C. are employed. The catalyst system is then ready to be charged to the reactor.

Optionally, prior to charging the reactor, the catalyst system can be mixed with an inert substance to dilute the catalyst system and decrease the rate of olefin dimerization. Any inert substance which has little or no catalytic activity in an olefin dimerization reaction can be used. One example of such an inert substance is glass beads. Another example is potassium carbonate extrudates with no alkali metal.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal, and promoter(s) which one may choose to employ will depend on a variety of variables such as for example, reactor configuration, reaction temperature and pressure, olefin feed employed, rate of olefin feed, and conversions desired.

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operation, although the catalysts of the invention are particularly well suited for continuous, fixed bed, operation. Suitable equipment, such as, for example, autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 500 to about 2,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors, such as, for example, the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 40 will be employed. A WHSV of about 1 to about 30 is preferred, with about 1 to about 20 WHSV most preferred for optimum catalyst productivity.

Products

The olefinic products of the invention have established utility in a wide variety of applications, such as, for example, as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

Example 1

(A) Water and Alcohol Catalyst Support Preparation

Twenty pounds of potassium carbonate ($K_2CO_3$) (JT Baker, ACS reagent grade) were added to a large Lancaster mix-muller. The amount of water added was adjusted to account for moisture in the $K_2CO_3$ such that the final mixture had 0.24 g $H_2O$/1 g $K_2CO_3$. The water was evenly added to the mix-muller over a time of about three (3) minutes. Then, n-propanol ($C_3OH_8$) (JT Baker, ACS reagent grade) was evenly added to the mix-muller over a time of about 5 minutes, such that the mix-muller had 0.16 g $C_3OH_8$/1 g $K_2CO_3$, water and alcohol mixture was mixed for 12 minutes, and then a cycle of 4.5 minutes of no mixing (stand time) and 0.5 minutes of mixing commenced and continued for 35 minutes thereafter.

The paste was fed to a 2¼ inch Bonnot single screw extruder, with a barrel temperature of 30° C. The extrudate was ⅛ inch diameter. The extrudate was vacuum dried at 315° F. (157° C.) overnight. The dried extrudate was calcined at 518° F. (270° C.) for 3 hours, under air, to form a support.

For impregnation, potassium was heated to 75° C. and the support was heated 100° C., under an inert atmosphere. Potassium was added to the support, with good mixing. Potassium impregnation, or loading, was 8 weight percent, based on the weight of the calcined support.

(B) Water Only Catalyst Support Preparation

The procedure of the Water and Alcohol Catalyst Support Preparation was followed exactly, except for two variations. The water/$K_2CO_3$ mixture comprised 0.27 g $H_2O$/1 g $K_2CO_3$. Secondly, no alcohol (n-propanol) was added to the mixture.

(C) Dimerization Reaction

The dimerization of propylene was carried out in a steam heated 316 stainless steel tubular reactor (⅜×20″). The catalyst system (50 grams) was loaded into the reactor. The contents of the tubular reactor were heated to a reaction temperature of about 160° C., at about 1600 psig, and propylene was pumped into the reactor with a weight hourly space velocity of 1.2. After about 1.5 hours of reaction time and each one hour thereafter for the following 6 hours, a sample was collected and analyzed by gas liquid chromatography (glc) from each run. Three runs were performed with each type of catalyst. The summarized results represent the average analysis of the last dimerization sample collected from each of the 3 runs (see Table I).

TABLE I

|  | Propylene Conversion, % | Selectivity to 4MP1, % | 4MP1/4MP2 |
|---|---|---|---|
| Water & Alcohol Extruded Support | 19.8 | 87.2 | 16 |
| Water Only Extruded Support | 20.3 | 87.5 | 17 |

The data show that there is no substantial difference in dimerization results between the two types of catalyst support preparation procedures. However, the use of alcohol requires additional solvent handling and recovery equipment, as well as significant safety precautions. Therefore, a catalyst support extruded using only water as a solvent is much more preferable for economic, as well as safety reasons.

Example II

Catalyst support was prepared by adding varying amounts of alkali metal carbonate to a small mix-muller. Sodium carbonate (Fisher, reagent grade) and cesium carbonate (Henley Chemicals, technical grade) were tested. Sodium carbonate ($Na_2CO_3$) has a solubility in cold water of 7.1 g $Na_2CO_3$/100 g $H_2O$. Cesium carbonate ($Cs_2CO_3$) has a solubility in cold water of 260.5 g $Cs_2CO_3$/100 g $H_2O$. Potassium carbonate has a solubility in cold water of 112 g $K_2CO_3$/100 g $H_2O$.

The paste was fed to a "BB-Gun Bonnot" single screw extruder, with a barrel temperature of 30° C., through a stainless steel die with 4 holes of ⅛ inch diameter. The extrudate was dried in a convection or vacuum oven overnight. The dried extrudate was calcined at 650° F. (343° C.), under air, for 30 minutes, to form a support.

The results of the extrusions are listed in Table II.

TABLE II

| Run | Alkali Metal Carbonate ($X_2CO_3$) | $gH_2O$/$gX_2CO_3$ | Extrudability | Drying Process | Dried Crush Strength, lbs. | Calcined Crush Strength, lbs. | Comments |
|---|---|---|---|---|---|---|---|
| 201 | $Na_2CO_3$ | 0.28 | yes | convection | 4.29 | 3.93 | extruded fairly well but rough extrudates |
| 202 | $Na_2CO_3$ | 0.30 | yes | convection | 5.37 | 3.25 | extruded fairly well, but rough extrudates |
| 203 | $Cs_2CO_3$ | 0.26 | no, too wet | — | — | — | made syrup-like liquid |
| 204 | $Cs_2CO_3$ | 0.11 | no, too dry | — | — | — | — |
| 205 | $Cs_2CO_3$ | 0.14 | yes, wet | convection* | — | — | melted in convection oven |
| 206 | $Cs_2CO_3$ | 0.11 | no, too dry | — | — | — | — |
| 207 | $Cs_2CO_3$ | 0.14 | yes | vacuum | 7.75 | 8.02 | extrudate was wet and sticky |
| 208 | $Cs_2CO_3$ | 0.12 | no, too dry | — | — | — | — |
| 209 | $Cs_2CO_3$ | 0.13 | no, too dry | — | — | — | — |
| 210 | $Cs_2CO_3$ | 0.13 | yes | vacuum | 4.66 | — | about one-half of feed formed extrudates |

*dried at 176° C., for 2 hours

The data in Table II show that sodium carbonate and cesium carbonate can be extruded from a water-only based paste. However, the sodium carbonate extrudates are inferior to potassium carbonate extrudates (see Example IV), in that sodium carbonate extrudates have a rough exterior and have relatively weak crush strengths. Cesium carbonate extrudates have acceptable crush strengths, compared to potassium carbonate extrudates, but cesium carbonate and water is difficult to extrude and the resultant extrudate cannot be vacuum dried.

Example III

Catalyst support was prepared by adding 20 pounds of potassium carbonate (JT Baker, ACS reagent grade) to a large Lancaster mix-muller. The amount of water added was adjusted to account for moisture in the $K_2CO_3$, such that the final mixture had 0.26 g $H_2O$/g $K_2CO_3$. The water, which had a temperature of 4° C., was evenly added to the mix-muller over a time of about 6 minutes. The total residence time of the $K_2CO_3$ and water in the mix-muller was 20 minutes after completion of the water addition.

The paste was fed to a 2¼ inch Bonnot single screw extruder, with a barrel temperature of 30° C., through a stainless steel die with 48 holes of ⅛ inch diameter. The extrudate was dried in a convection oven at 350° F. (177° C.), under air, for 3 hours. The dried extrudate was calcined at 650° F. (343° C.), under air, for 30 minutes, to form a support.

Catalysts with various levels of elemental sodium and elemental potassium were prepared by weighing out solid sodium and potassium, and then melting them together.

For impregnation, elemental alkali metal(s) was heated to 75° C. and the support was heated to 100° C., under an inert atmosphere. The molten elemental alkali metal was added to the support, with good mixing. Elemental alkali metal(s) impregnation, or loading, was 4 weight percent, based on the weight of the calcined support.

The dimerization of propylene was carried out in a steam heated 316 stainless steel tubular reactor (¼"×20"). The catalyst system (40 grams) was loaded into the reactor and was bounded above and below by a total of about 10 g of glass beads. The contents of the tubular reactor were heated to a reaction temperature of about 150° C., at about 1600 psig, and propylene was pumped into the reactor with a weight hourly space velocity of 3.75. After about 1.5 hours of reaction time and each one hour thereafter for the following 10 hours, a sample was collected and analyzed by gas liquid chromatography (glc). Three runs were performed with each type of catalyst. The summarized results represent the average analysis of the last dimerization sample collected from each of the three runs (see Table III).

TABLE III

| Run | % Na* | % K* | 4MP1/4MP2 |
|-----|-------|------|-----------|
| 301 | 0     | 100  | 45        |
| 302 | 10    | 90   | 45        |
| 303 | 15    | 85   | 37        |
| 304 | 20    | 80   | 38        |
| 305 | 25    | 75   | 35        |

*percent by weight, based on the total weight of the Na/K blend

The 4MP1 (4-methylpentene-1) to 4MP2 (4-methylpentene-2) ratio is critical because 4MP2 is undesirable, and is very difficult to separate from 4MP1. The data was obtained from the plots of ratio versus selectivity. By comparing the performance at equal selectivity and conversion, a fair comparison of the effects can be given. A selectivity of about 90% 4MP1 was used because that was an average selectivity.

The data show that at 10% Na/90% K (Run 302) there was no loss of selectivity compared to pure potassium (Run 301). While not wishing to be bound by theory, this is probably due to the exchange of sodium of the elemental alkali metal with potassium ions from the potassium carbonate support producing additional potassium and generating sodium ions. At higher sodium levels, this exchange of sodium with potassium is probably much less effective.

Example IV

The following Example describes the variable (parameter) screening process to determine the dominant variable (parameter) factors and the optimization process of the dominant factors of the catalyst support preparation procedure. Unless otherwise specifically stated, catalyst support was prepared as follows.

Seventy-five pounds of potassium carbonate ($K_2CO_3$) (JT Baker, ACS reagent grade) were added to a large Lancaster mix-muller. The amount of water added was adjusted to account for moisture in the $K_2CO_3$, such that the final mixture had from 0.24 g $H_2O$ to 0.28 g $H_2O$ per gram $K_2CO_3$. The water was evenly added, i.e. sprayed, onto the mix-muller at a rate of 2.6 lbs $H_2O$/min. Water addition temperature ranged from 32° F. (0° C.), i.e., ice water, to 68° F. (20° C.) during the screening process and from 32° F. (0° C.), i.e., ice water, to 40° F. (4° C.) during the optimization process. The mixing time ranged from 20 to 60 minutes.

The paste was fed to a 2¼ inch Bonnot single screw extruder. The extrudate was vacuum or convection dried and then calcined, under air, to form a support.

Tables IV and V, below, give the parameters and ranges, if appropriate, for the variable (parameter) screening (Table IV) and optimization (Table V) analyses.

TABLE IV

| Parameter | Experimental Design Limits Low | High |
|-----------|-------|------|
| Water to potassium carbonate (dry) ratio | 0.25 | 0.27 |
| Mix-muller roller height above pan (inches) | 0.25 | 1 |
| Water addition temperature (°F.) | 32 | 68 |
| Mixing time after water addition (minutes) | 20 | 60 |
| % Agitation during mixing | 10 | 100 |
| Covering of prepared paste | No | Yes |
| Aging after mixing (minutes) | 0 | 120 |
| Die Cooling | No | Yes |
| 2¼" Bonnot Extruder auger rpm | 40 | 60 |
| Extruder barrel coolant temperature (°F.) | 86 | 122 |
| K-Tron model 7821 mechanical feeder | 35 | 55 |

| Constants | Value |
|-----------|-------|
| Batch Size (1) | 75 lbs. $K_2CO_3$ |
| Water delivery rate | 2.6 lbs./min. |
| Die holes (2) | 40¼" diameter holes |
| Die thickness | 0.25 inches |
| Convection oven temperature | 350° F. |
| Convection drying time (3) | 3 hours |
| Calcining temperature | 650° F. |
| Calcining time | 30 minutes |

TABLE V

| Parameter | Experimental Design Limits Low | High |
|-----------|-------|------|
| Water to potassium carbonate (dry) ratio | 0.24 | 0.28 |
| Mixing time after water addition (minutes) | 20 | 60 |
| % Agitation during mixing | 10 | 100 |
| 2¼" Bonnot Extruder auger rpm | 40 | 60 |
| Convection Drying Temperature (°F.) | 250 | 450 |
| Calcining Temperature (°F.), (1) | 500 | 650 |
| Calcining Time (min.), (2) | 30 | 180 |

| Constants | Value |
|-----------|-------|
| Batch Size | 75 lbs. $K_2CO_3$ |
| Mix-muller roller height above pan (inches) | 1 |
| Water delivery rate | 2.6 lbs./min. |
| Water addition temperature (°F.) | 32-40 |
| Covering of prepared paste | Yes |
| Aging after mixing (min.) | 0 |
| Die Cooling | Yes |
| Die holes | 48¼" diameter holes |
| Die thickness | 0.25 inches |
| Extrude barrel coolant temperature (°F.) | 86 |
| K-Tron model 7821 mechanical feeder | 55 |
| Convection oven temperature | 350° F. |
| Convection drying time | 3 hours |

Notes:
(1) All samples were calcined at both calcining temperatures.
(2) All samples were calcined at both calcining times.

A multiple linear regression analysis, Systat ®, was performed by computer to determine the dominant variable (parameter) factors. The Systat ® computer program is commercially available from Systat, Inc., Evanston, IL.

The dominant variable (parameter) factors analyzed are those listed as "Parameters" in Table IV. Based on the multiple linear regression analysis, the most important variables are:

1) $H_2O$ to $K_2CO_3$ Ratio
2) Mixer Residence Time
3) Fraction of Active Mixing
4) Extruder Auger rpm
5) Drying Temperature These five variables were studied for optimization. The analytical results, in Tables VI and VII below, were also analyzed with Systat ®, a multiple linear regression analysis computer program, to determine the true optimization. The data in Table VI provides support and catalyst properties. The data in Table VII provides support and catalyst properties, as well as propylene dimerization process results. The dimerization results were obtained under dimerization conditions similar to those previously described in Example I.

TABLE VI

| | Mixer | Active | Extruder | Drying | | Dried | Bulk Density |
|---|---|---|---|---|---|---|---|

TABLE VI-continued

| Run | gH₂O/ gK₂CO₃ | Residence Time (min.) | Mixing, % time | Auger rpm | Temp (°F.) | % Fines by weight[a] | Crush (lbs)[a][c] | (cc/g)[a] Loose | (cc/g)[a] Packed |
|---|---|---|---|---|---|---|---|---|---|
| 401 | 0.26 | 40 | 50 | 50 | 250 | 3.4 | 8.8 | 0.72 | 0.81 |
| 402 | 0.27 | 20 | 10 | 60 | 400 | 2.7 | 5.0 | 0.47 | 0.57 |
| 403 | 0.26 | 40 | 100 | 50 | 350 | 4.5 | 8.0 | 0.62 | 0.73 |
| 404 | 0.26 | 40 | 50 | 60 | 350 | 3.8 | 7.5 | 0.67 | 0.80 |
| 405 | 0.27 | 60 | 10 | 40 | 400 | 2.9 | 5.6 | 0.41 | 0.54 |
| 406 | 0.25 | 60 | 100 | 40 | 400 | 7.4 | 4.5 | 0.56 | 0.64 |
| 407 | 0.25 | 20 | 10 | 40 | 400 | 4.1 | 6.8 | 0.64 | 0.74 |
| 408 | 0.26 | 90 | 50 | 50 | 350 | 5.1 | 7.3 | 0.59 | 0.71 |
| 409 | 0.27 | 60 | 100 | 40 | 300 | 3.9 | 8.9 | 0.7 | 0.81 |
| 410 | 0.27 | 60 | 100 | 60 | 400 | 5.2 | 5.5 | 0.53 | 0.64 |
| 411 | 0.25 | 20 | 100 | 40 | 300 | 5.4 | 8.4 | 0.71 | 0.80 |
| 412 | 0.26 | 20 | 100 | 60 | 300 | 4.1 | 7.7 | 0.68 | 0.79 |
| 413 | 0.26 | 60 | 100 | 60 | 300 | 8.7 | 8.4 | 0.65 | 0.76 |
| 414 | 0.26 | 40 | 20 | 50 | 350 | 2.4 | 6.8 | 0.47 | 0.62 |
| 415 | 0.24 | 10 | 50 | 50 | 350 | 3.4 | 7.3 | 0.63 | 0.71 |
| 416 | 0.28 | 40 | 50 | 30 | 350 | 4.7 | 7.7 | 0.62 | 0.74 |
| 417 | 0.25 | 40 | 50 | 50 | 350 | 8.2 | 7.0 | 0.58 | 0.71 |
| 418 | 0.28 | 40 | 50 | 50 | 350 | 0 | 5.5 | 0.35 | 0.43 |
| 419 | 0.25 | 60 | 10 | 60 | 400 | 6.2 | 7.2 | 0.6 | 0.75 |
| 420 | 0.25 | 60 | 10 | 40 | 300 | 5.3 | 8.0 | 0.67 | 0.80 |
| 421 | 0.25 | 20 | 100 | 60 | 400 | 5.4 | 6.7 | 0.63 | 0.74 |
| 422 | 0.27 | 60 | 10 | 60 | 300 | 3.9 | 9.1 | 0.5 | 0.67 |
| 423 | 0.27 | 20 | 10 | 40 | 300 | 4.2 | 8.5 | 0.67 | 0.81 |
| 424 | 0.25 | 20 | 10 | 60 | 300 | 7.0 | 8.2 | 0.68 | 0.78 |
| 425 | 0.27 | 20 | 100 | 40 | 400 | 4.1 | 6.4 | 0.5 | 0.61 |
| 426 | 0.26 | 40 | 50 | 50 | 450 | 5.5 | 6.7 | 0.56 | 0.67 |
| 427 | 0.26 | 40 | 50 | 55 | 350 | 4.8 | 7.8 | 0.61 | 0.74 |
| 428 | 0.26 | 40 | 75 | 60 | 350 | 5.3 | 8.6 | 0.66 | 0.77 |
| 429 | 0.26 | 60 | 10 | 60 | 275 | 4.0 | 9.4 | 0.72 | 0.85 |

| Run | K₂CO₃ lbs Extruded | Extrusion Rate (lbs/min) | % Full Impreg[b] | % Partial Impreg[b] | % No Impreg[b] |
|---|---|---|---|---|---|
| 401 | 75 | 0.65 | 7.5 | 30 | 62.5 |
| 402 | 75 | 1.15 | 7.5 | 47.5 | 45 |
| 403 | 75 | 0.75 | 25 | 45 | 30 |
| 404 | 75 | 0.62 | 0 | 0 | 100 |
| 405 | 75 | 0.48 | 0 | 0 | 100 |
| 406 | 75 | 0.64 | 27.5 | 47.5 | 25 |
| 407 | 75 | 0.83 | 32.5 | 60 | 7.5 |
| 408 | 75 | 0.62 | 37.5 | 60 | 2.5 |
| 409 | 75 | 0.59 | 5 | 27.5 | 67.5 |
| 410 | 75 | 0.67 | 30 | 60 | 10 |
| 411 | 56 | 0.56 | 35 | 45 | 20 |
| 412 | 75 | 0.73 | 0 | 20 | 80 |
| 413 | 75 | 0.65 | 20 | 25 | 55 |
| 414 | 75 | 0.94 | 100 | 0 | 0 |
| 415 | 75 | 0.74 | 85 | 15 | 0 |
| 416 | 75 | 0.60 | 65 | 30 | 5 |
| 417 | 75 | 0.68 | 62.5 | 35 | 2.5 |
| 418 | 75 | 0.56 | 0 | 50 | 50 |
| 419 | 75 | 0.76 | 30 | 70 | 0 |
| 420 | 75 | 0.73 | 25 | 50 | 25 |
| 421 | 75 | 0.73 | 55 | 45 | 0 |
| 422 | 75 | 0.71 | 0 | 40 | 60 |
| 423 | 75 | 0.88 | 0 | 20 | 80 |
| 424 | 14 | 0.64 | 75 | 25 | 0 |
| 425 | 75 | 0.67 | 40 | 60 | 0 |
| 426 | 75 | 0.71 | 45 | 50 | 5 |
| 427 | 75 | 0.75 | 47.5 | 42.5 | 10 |
| 428 | 75 | 0.75 | — | — | — |
| 429 | 75 | 0.83 | — | — | — |

[a]Determined on dried, non-calcined support.
[b]Support Calcined at 500° F. (260° C.) for 30 minutes prior to impregnation.
[c]Fines are those particles that are less than 10 mesh (<1.65 mm) after extrusion and drying.

TABLE VII

| Run | gH₂O/ gK₂CO₃ | Mixer Residence Time (min.) | Active Mixing, % time | Extruder Auger rpm | Drying Temp (°F.) | % Full Impreg[a] | % Partial Impreg[a] | % No Impreg[a] | Propylene Conversion, % | 4-MP-1 Selectivity, % | 4MP1 to 4MP2 Ratio |
|---|---|---|---|---|---|---|---|---|---|---|---|
| 430 | 0.26 | 40 | 50 | 50 | 250 | 40 | 32.5 | 27.5 | 5 | 87 | 18.5 |
| 431 | 0.27 | 20 | 10 | 60 | 400 | 92.5 | 5 | 2.5 | 25 | 88 | 29.0 |
| 432 | 0.26 | 40 | 100 | 50 | 350 | 47.5 | 40 | 12.5 | — | — | — |
| 433 | 0.26 | 40 | 50 | 60 | 350 | 75 | 22.5 | 2.5 | 30 | 90 | 25 |
| 434 | 0.27 | 60 | 10 | 40 | 400 | 23.3 | 53.4 | 23.3 | 13 | 87 | 18 |
| 435 | 0.25 | 60 | 100 | 40 | 400 | 27.5 | 55 | 17.5 | 44 | 89 | 25.6 |

TABLE VII-continued

| Run | gH$_2$O/ gK$_2$CO$_3$ | Mixer Residence Time (min.) | Active Mixing, % time | Extruder Auger rpm | Drying Temp (°F.) | % Full Impreg[a] | % Partial Impreg[a] | % No Impreg[a] | Propylene Conversion, % | 4-MP-1 Selectivity, % | 4MP1 to 4MP2 Ratio |
|---|---|---|---|---|---|---|---|---|---|---|---|
| 436 | 0.25 | 20 | 10 | 40 | 400 | 42.5 | 45 | 12.5 | 20 | 89 | 21.5 |
| 437 | 0.26 | 90 | 50 | 50 | 350 | 72.5 | 27.5 | 0 | 36 | 90 | 21.1 |
| 438 | 0.27 | 60 | 100 | 40 | 300 | 45 | 50 | 5 | 6 | 89 | 25.7 |
| 439 | 0.27 | 60 | 100 | 60 | 400 | 95 | 15 | 0 | 39 | 88 | 17.4 |
| 440 | 0.25 | 20 | 100 | 40 | 300 | 70 | 30 | 0 | 20 | 90 | 25.9 |
| 441 | 0.27 | 20 | 100 | 60 | 300 | 35 | 50 | 15 | 4 | 88 | 25.2 |
| 442 | 0.25 | 60 | 100 | 60 | 300 | 40 | 30 | 30 | 5 | 88 | 28.1 |
| 443 | 0.26 | 40 | 2 | 50 | 350 | 75 | 25 | 0 | 36 | 89 | 17.9 |
| 444 | 0.26 | 10 | 50 | 50 | 350 | 82.5 | 17.5 | 0 | 37 | 88 | 19.3 |
| 445 | 0.26 | 40 | 50 | 30 | 350 | 65 | 35 | 0 | 27 | 89 | 21.0 |
| 446 | 0.24 | 40 | 50 | 50 | 350 | 65 | 35 | 0 | 40 | 89 | 21.7 |
| 447 | 0.28 | 40 | 50 | 50 | 350 | 10 | 60 | 30 | 18 | 89 | 24.2 |
| 448 | 0.25 | 60 | 10 | 60 | 400 | 55 | 45 | 0 | 26 | 90 | 22.1 |
| 449 | 0.25 | 60 | 10 | 40 | 300 | 55 | 35 | 10 | 5 | 91 | 41.4 |
| 450 | 0.25 | 20 | 100 | 60 | 400 | 60 | 40 | 0 | 28 | 90 | 23 |
| 451 | 0.27 | 60 | 10 | 60 | 300 | 40 | 50 | 10 | 11 | 88 | 22 |
| 452 | 0.27 | 20 | 10 | 40 | 300 | 0 | 20 | 80 | 13 | 89 | 24.4 |
| 453 | 0.25 | 20 | 10 | 60 | 300 | 80 | 20 | 0 | 31 | 90 | 20.0 |
| 454 | 0.27 | 20 | 100 | 40 | 400 | 75 | 25 | 0 | 24 | 89 | 21.8 |
| 455 | 0.26 | 40 | 50 | 50 | 450 | 20 | 80 | 0 | 23 | 90 | 26.8 |
| 456 | 0.26 | 40 | 50 | 55 | 350 | 10 | 35 | 55 | 40 | 87 | 16.0 |
| 457 | 0.26 | 40 | 75 | 60 | 350 | — | — | — | 20 | 88 | 24.0 |
| 458 | 0.26 | 60 | 10 | 60 | 275 | — | — | — | 10 | 88 | 23.4 |

[a]Support calcined at 650° F. (343° C.) for 30 minutes prior to impregnation.

The multiple linear regression analysis performed on the experimental data given in Tables VI and VII resulted in optimum conditions needed to perform an efficient extrusion, as well as produce the best overall catalyst and catalyst support. The results, as determined by the Systat ® program, given in Table VIII below, are given as ranges in order to account for reasonable deviations from the computer-generated optimized conditions.

TABLE VIII

| Parameter | Broad Range | Optimized Range | Computer-Generated Optimized Condition |
|---|---|---|---|
| gH$_2$O/gK$_2$CO$_3$ | 0.23–0.29 | 0.25–0.27 | 0.26 |
| Total mixing time (min.) after initial water addition | up to one (1) hour | 20–40 min. | 20 min. |
| Active mixing, % time | 1–50 | 5–20 | 10% |
| Extruder auger, rpm | 20–100 | 45–70 | 60 rpm |
| Convection Drying temp., °F. (°C.) | 212–500° F. (100–260° C.) | 293–401° F. (145–205° C.) | 350° F. (177° C.) |

While none of the Runs correspond exactly to the computer-generated optimized conditions, Runs 414 and 453 correspond very closely to the computer-generated optimized conditions. The only variances are gH$_2$O/gK$_2$CO$_3$ of 0.25 and drying temperature of 300° F. Runs 414 and 453 show good elemental alkali metal (potassium) impregnation, as well as good propylene conversion, 4MP1 selectivity, and 4MP1/4MP2 ratio.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process to prepare a catalyst support comprising the steps of:
    a) preparing a thick paste comprising potassium carbonate and water, wherein said water to potassium carbonate weight ratio is within a range of about 0.23 grams per gram to about 0.29 grams water per gram potassium carbonate;
    b) extruding said paste to form an extrudate; and
    c) drying said extrudate to produce a dried extrudate.

2. A process according to claim 1 wherein said potassium carbonate and water are mulled for a time within the range of up to about 60 minutes prior to extrusion.

3. A process according to claim 2 wherein a mixing device is operated for about 1 to about 50 percent of the total time said potassium carbonate and water are in contact in a mixing vessel.

4. A process according to claim 1 wherein said potassium carbonate and water are mulled at a temperature within the range of about 0° to about 25° C.

5. A process according to claim 1 wherein said potassium carbonate and water are aged for a time of up to about 24 hours after mulling.

6. A process according to claim 1 wherein said paste is extruded through an extruder with a barrel temperature within the range of about 0° to about 60° C.

7. A process according to claim 1 wherein said drying is a vacuum drying process to produce a vacuum dried extrudate.

8. A process according to claim 7 wherein said vacuum drying is done at a temperature within the range of about 145° to about 170° C.

9. A process according to claim 7 wherein the vacuum dried extrudate comprises from about 0 to about 3 weight percent water, based on the total weight of the extrudate.

10. A process according to claim 1 wherein said drying is a convection drying process to produce a convection dried extrudate.

11. A process according to claim 10 wherein said convection drying process is at a temperature within the range of about 100° to about 260° C.

12. A process according to claim 10 wherein the convection dried extrudate comprises from about 0 to about 10 weight percent water, based on the total weight of the extrudate.

13. A process according to claim 1 further comprising calcining the dried extrudate to produce a calcined extrudate.

14. A process according to claim 13 wherein said calcining occurs at a temperature within the range of about 260° to about 400° C.

15. A process according to claim 13 to produce a catalyst system comprising contacting the calcined extrudate with at least one elemental alkali metal.

16. A process according to claim 15 wherein said elemental alkali metal is selected from the group consisting of lithium, sodium, potassium, rubidium, cesium, and mixtures thereof.

17. A process according to claim 15 wherein said elemental alkali metal comprises from about 1 to about 20 weight of the catalyst system, based on the weight of the support.

18. A process to prepare a catalyst support comprising the steps of:
a) preparing a thick paste comprising potassium carbonate and water, wherein the water to potassium carbonate weight ratio is within a range of about 0.23 grams per gram to about 0.29 grams water per gram potassium carbonate;
b) mixing said thick paste for a time within the range of up to 60 minutes, wherein a mixing device is operated for about 1 to about 50 percent of the total time said potassium carbonate and water are in contact in a mixing vessel, at a temperature within the range of about 0° to about 25° C.;
c) extruding said paste through an extruder to form an extrudate, wherein said extruder barrel temperature is within the range of about 0° to about 60° C.;
d) drying said extrudate at a temperature within the range of about 100° to about 260° C. to produce a dried extrudate, for a time sufficient such that the dried extrudate comprises from about 0 to about 10 weight of the extrudate;
e) calcining the dried-extrudate at a temperature within the range of from about 260° to about 400° C. to produce a calcined extrudate.

19. A process according to claim 18 comprising contacting said catalyst support with an elemental alkali metal selected from the group consisting of sodium, potassium, and mixtures thereof to form a catalyst system.

* * * * *

UNITED STATES PATENT AND TRADEMARK OFFICE
CERTIFICATE OF CORRECTION

PATENT NO. : 5,202,298

DATED : April 13, 1993

INVENTOR(S) : Paul F. Schubert et al

It is certified that error appears in the above-identified patent and that said Letters Patent is hereby corrected as shown below:

On the title page, item (54), after "PREPARING" and before "CARBONATE" insert --- POTASSIUM ---.

Column 1, line 2 of the title, after "PREPARING" and before "CARBONATE" insert --POTASSIUM--.

Signed and Sealed this

Fifteenth Day of March, 1994

Attest:

BRUCE LEHMAN

Attesting Officer   Commissioner of Patents and Trademarks